United States Patent [19]

Yahagi et al.

[11] Patent Number: 4,613,879
[45] Date of Patent: Sep. 23, 1986

[54] CHROMOGENIC RECORDING MATERIALS

[75] Inventors: Masakichi Yahagi, Tokyo; Tetsuo Igaki, Kawagoe; Sinzi Yoshinaka, Iwatsuki; Kousaku Morita, Saitama; Morikuni Saitō, Tokyo; Kimiaki Kinoshitā, Kitamoto, all of Japan

[73] Assignee: Shin Nisso Kako Co., Ltd., Tokyo, Japan

[21] Appl. No.: 601,568

[22] Filed: Apr. 18, 1984

[30] Foreign Application Priority Data

Apr. 26, 1983 [JP] Japan .................. 58-72080

[51] Int. Cl.$^4$ .............. B41M 5/16; B41M 5/18; B41M 5/22
[52] U.S. Cl. .................. 346/209; 346/217; 346/221; 427/151
[58] Field of Search .............. 346/209, 216, 217, 221, 346/225

[56] References Cited

U.S. PATENT DOCUMENTS

| 2,548,366 | 4/1951 | Green et al. | 346/200 |
| 2,800,458 | 7/1957 | Green | 346/200 |
| 3,681,390 | 8/1972 | Lin | 260/335 |
| 3,746,562 | 7/1973 | Lin | 117/36.2 |

FOREIGN PATENT DOCUMENTS 0208092 12/1983 Japan .................. 346/221

Primary Examiner—Bruce H. Hess
Attorney, Agent, or Firm—Abelman Frayne Rezac & Schwab

[57]  ABSTRACT

This invention relates to chromogenic recording materials comprising as a chromogenic substance 3-N-isobutylethylamino-6-methyl-7-phenylaminofluoran of the following formula (I)

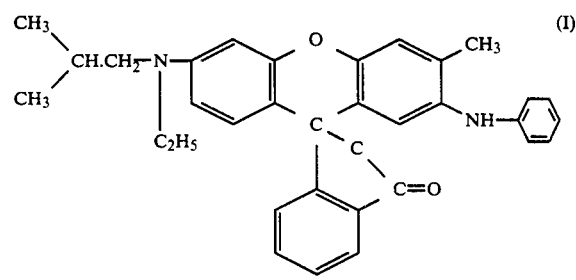

9 Claims, No Drawings

CHROMOGENIC RECORDING MATERIALS

FIELD OF THE INVENTION

The fluoran compound of the invention represented by the formula (I) is a substantially colorless substance by itself. But this compound has the capability of quickly developing a blackish purple to black color upon intimate contact with electron acceptors such as terra abla, clays, phenol-formaldehyde resins, bisphenol A (4,4'-isopropylidene diphenol) or benzyl p-hydroxybenzoate. Because of such property, the fluoran compound may be utilized as a black color-producing chromogenic substance in the chromogenic recording materials such as heat-sensitive recording papers or pressure-sensitive copying papers.

At present, as the black color-producing chromogenic substances in the chromogenic recording materials are used widely two types of compounds, i.e., 3-diethylamino-6-methyl-7-phenylaminofluoran of the formula (II) (U.S. Pat. No. 3,681,390)

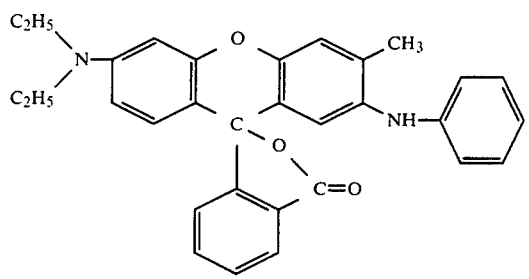

and 3-N-methylcyclohexylamino-6-methyl-7-phenylaminofluoran of the formula (III) (Japanese Patent Publication No. 23204/1976)

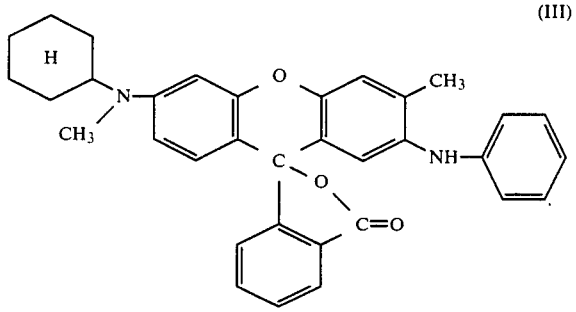

However, there is an increased demand of heat-sensitive recording papers of a high color-developing rate in association with the development of facsimiles of the heat-sensitive type with which heat-sensitive recording papers are mainly used. The above two types of fluoran compounds have not satisfied this demand.

The fluoran compound of the invention is a novel substance which can satisfy the above demand and has the feature that a mixture of this fluoran compound and a developer of, for example, bisphenol A has a much higher color density at low temperatures of 85° to 100° C. than similar mixtures of the compound of the formula (II) or (III).

In Japanese Laid-open Patent Application No. 34909/1979, a fluoran compound of the formula (IV) is disclosed as exhibiting a higher level of color formation at low temperatures than known fluoran compounds

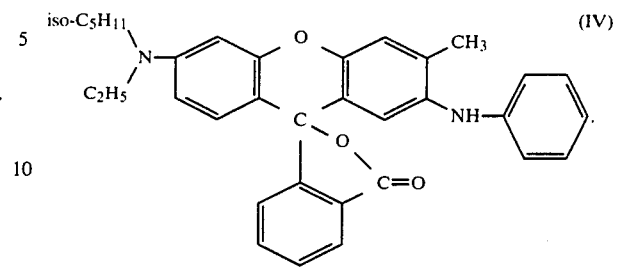

However, the compound of the invention has better black color developability than the above-noted fluoran compound. These are summarized in Table 1 for comparison.

TABLE 1

| Compound | Color Formation Temperature (°C.) | | | | | | | | |
| --- | --- | --- | --- | --- | --- | --- | --- | --- | --- |
| | 70 | 80 | 85 | 90 | 95 | 100 | 105 | 110 | 140 |
| I | 0.23 | 0.26 | 0.42 | 0.72 | 1.10 | 1.16 | 1.19 | 1.21 | 1.25 |
| II | 0.18 | 0.19 | 0.27 | 0.37 | 0.70 | 0.99 | 1.10 | 1.18 | 1.24 |
| III | 0.18 | 0.19 | 0.25 | 0.35 | 0.68 | 0.96 | 1.07 | 1.17 | 1.23 |
| IV | 0.17 | 0.17 | 0.27 | 0.50 | 0.93 | 1.12 | 1.16 | 1.19 | 1.24 |

A similar comparison is shown in Table 2 in which benzyl p-hydroxybenzoate is used as the developer.

TABLE 2

| Compound | Color Formation Temperature (°C.) | | | | | | |
| --- | --- | --- | --- | --- | --- | --- | --- |
| | 70 | 75 | 80 | 85 | 90 | 95 | 100 |
| I | 0.24 | 0.72 | 1.16 | 1.30 | 1.32 | 1.33 | 1.33 |
| II | 0.15 | 0.23 | 0.77 | 1.18 | 1.22 | 1.28 | 1.28 |
| III | 0.17 | 0.29 | 0.71 | 1.15 | 1.20 | 1.27 | 1.28 |
| IV | 0.13 | 0.46 | 0.94 | 1.22 | 1.27 | 1.29 | 1.31 |

In Table 1, the values indicate color densities, at the respective temperatures, of the heat-sensitive recording papers made in Example 1 and Comparative Example 1. Similarly, the values in Table 2 indicate color densities, at the respective temperatures, of heat-sensitive recording papers made in Example 2 and Comparative Example 2. For the color development, a Dry Heating Tester (manufactured and sold by Kishino Science Machinery Co., Ltd.) was used for heating. The color density was measured using the Macbeth reflection densitometer. Larger values for the color density show deeper hues of color.

The results of Table 1 reveal that when bisphenol A is used as the developer, the fluoran compound of the invention has better color developability particularly at temperatures of about 85° to 100° C. than the known fluoran compounds of similar structures. Likewise, Table 2 demonstrates that when benzyl p-hydroxybenzoate is used as the developer, the fluoran compound of the invention has much more excellent color developability than the other fluoran compounds at temperatures of 75° to 90° C. These facts indicate that the fluoran compound of the invention is a very favorable chromogenic substance for heat-sensitive recording paper which is used in high speed facsimiles.

The fluoran compound of the invention has not only such an excellent color developability as described above, but also good resistance against light, stain due to cosmetic creams, and high temperature and high humidity conditions concerning its developed color.

Further, heat-sensitive recording papers using the fluoran compound have the prominent feature that even immediately after manufacture of the heat-sensitive recording papers or even when preserved over a long term under high temperature and high humidity conditions or when exposed to light on the coated surface, they suffer only an extremely small degree of soiling on the chromogenic surface thereof.

The manner of making heat-sensitive recording papers using the fluoran compound of the invention is similar to the case where known fluoran compounds are used. For instance, fine particles of a fluoran compound of the invention and fine particles of a developer are dispersed in an aqueous solution of water-soluble binder and the resulting suspension is coated onto paper and dried to obtain a heat-sensitive recording paper with excellent color developability. In case where sensitizers are added to the suspension, highly sensitive heat-sensitive recording papers may be obtained. The suspension may further comprise any known ingredients such as fillers, dispersants, antioxidants, de-sensitizers, anti-tack agents, defoamers, light stabilizers, fluorescent brightening agents and the like.

The developers useful in the present invention may include, aside from the above-noted bisphenol A and benzyl 4-hydroxybenzoate, bisphenol compounds such as 4,4'-secondary-butylidene bisphenol, 4,4'-cyclohexylidene bisphenol, 2,2'-dihydroxydiphenyl, and the like; 4-hydroxybenzoic acid esters such as ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate, diphenylmethyl 4-hydroxybenzoate, pentamethylene-bis(4-hydroxybenzoate) and the like; hydroxysulfones such as 4-hydroxy-4'-methyldiphenylsulfone, 4-hydroxy-4'-isopropoxydiphenylsulfone, 4-hydroxy-4'-butoxydiphenylsulfone and the like; 4-hydroxyphthalic acid diesters such as dimethyl 4-hydroxyphthalate, dicyclohexyl 4-hydroxyphthalate, diphenyl 4-hydroxyphthalate and the like; and hydroxyacetophenone, p-phenylphenol, benzyl 4-hydroxyphenylacetate, p-benzylphenol, hydroquinone monobenzyl ether and the like.

The water-soluble binders include, for example, polyvinyl alcohol, hydroxyethyl cellulose, carboxymethyl cellulose, styrene-maleic anhydride copolymer, styrenebutadiene copolymer emulsion, vinyl acetate-maleic anhydride copolymer emulsion, polyacrylates, polyacrylamides, starches, casein, gum arabic and the like.

Examples of sensitizers include higher fatty acids amides, benzamide, stearic acid anilide, acetoacetic acid anilide, thioacetoanilide, dimethyl phthalate, dibenzyl terephthalate, dibenzyl isophthalate, bis(tert-butylphenol)s, diethers of bisphenol S, 4,4'-dimethoxydiphenyl sulfone, 4-iso-propoxy-4'-n-butoxydiphenyl sulfone, 4,4'-di-n-butoxydiphenyl sulfone, 4,4'-n- (or iso-) pentyloxydiphenyl sulfone, diphenylamine, carbazole, 2,3-di-m-tolylbutane, 4,4'-dimethylbiphenyl, di-beta-naphthylphenylenediamine and the like.

The fillers are, for example, clay, talc, kaolin, titanium oxide, calcium carbonate, magnesium carbonate, barium sulfate, magnesium silicate, aluminium silicate and the like.

The dispersants are, for example, sodium tripolyphosphate, sodium dodecylbenzenesulfonate, sodium salt of lauryl alcohol sulfate, metal salts of fatty acids and the like.

The antioxidants are, for example, 2,2'-methylene-bis(4-methyl-6-tert-butylphenol), 2,2'-methylene-bis(4-ethyl-6-tert-butylphenol), 4,4'-propylmethylene-bis(3-methyl-6-tert-butylphenol), 4,4'-thio-bis(2-tert-butyl-5-methylphenol) and the like.

The de-sensitizers are, for example, higher aliphatic alcohols, polyethyleneglycols, derivatives of guanidine and the like.

The anti-tack agents are, for example, stearic acid, zinc stearate, calcium stearate, carnauba wax, paraffin wax, ester wax and the like.

The fluoran compound of the invention is very excellent as a color-forming dye for heat-sensitive recording papers as described before and may also be excellent when used in pressure-sensitive copying paper. For instance, a coated back paper (CB) for pressure-sensitive copying purposes made in Example 3 assumes a yellowish brown color only in a very slight degree upon exposure of its capsule-coated surface to sunlight. Further, the black color developed on a phenol-formaldehyde resin-coated surface or the purplish black color developed on a clay-coated surface of coated front paper (CF) by intimate contact with the CB is excellent in light fastness.

The fluoran compound of the invention is more readily soluble than the compounds II and III in organic solvents such as, for example, alkylnaphthalenes and alkyl diphenyls which are used for the manufacture of pressure-sensitive copying paper. This permits easy manufacture of pressure-sensitive copying paper.

The developers used in combination with the fluoran compound of the invention for manufacture of pressure-sensitive copying paper may be any known materials. Examples of the materials include inorganic acidic substances such as terra abla, activated clay, attapulgite, bentonite, colloidal silica, aluminium silicate, magnesium silicate, zinc silicate, tin silicate, calcined clay, talc and the like; aliphatic carboxylic acids such as oxalic acid, maleic acid, tartaric acid, citric acid, succinic acid, stearic acid and the like; aromatic carboxylic acids such as benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid, 3-phenyl-5-($\alpha,\alpha$-dimethylbenzyl)salicylic acid, 3,5-di-($\alpha$-methylbenzyl)salicylic acid, 2-hydroxy-1-benzyl-3-naphthoic acid and the like; salts of the above-indicated aromatic carboxylic acids and metals such as zinc, magnesium, aluminium, titanium and the like; phenolic resins such as p-phenylphenolformaldehyde resin, p-butylphenol-acetylene resin and the like, and mixtures of these phenolic resins and the metal salts of the aromatic carboxylic acids.

The color formation upon intimate contact of the present fluoran compound with a developer also takes place on such substrates other than paper as noted above, such as synthetic fiber fabric, non-woven fabric, synthetic paper or synthetic resin sheet (e.g., transparent polythylene sheet).

The fluoran compound of the invention is prepared by reacting 1 mole of a benzoic acid derivative of the formula (V)

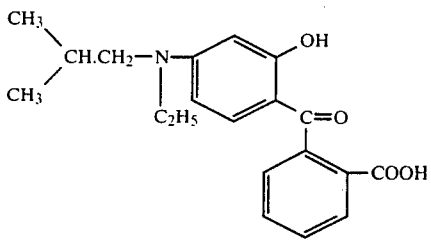

(V)

with about 1 mole of a diphenylamine derivative of the formula

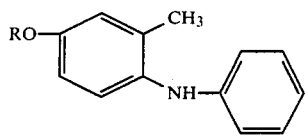

(in which R represents hydrogen or a lower alkyl group).

The benzoic acid derivative of formula (V) is prepared by reacting 1 mole of an m-aminophenol derivative of the formula

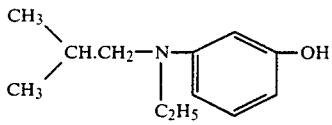

with about 1 mole of phthalic anhydride. This reaction is caused to proceed, for example, by heating both the compounds in a solvent such as toluene, tetrachloroethylene or 1,1,1-trichloroethane. The reaction system is conveniently heated to a refluxing temperature of the solvent used and thus the heating temperature may vary largely depending on the type of solvent and the concentration of the reaction solution. The temperature is generally in the range of 90° to 140° C. The reaction time is greatly influenced by the heating temperature and is ordinarily in the range of 4 to 20 hours. If necessary, acidic substances including Lewis acids such as anhydrous zinc chloride may be added as a catalyst. The m-aminophenol derivative as described above is prepared, for example, by subjecting m-isobutyl-aminophenol, obtained by reaction between resorcin and isobutylamine, to N-ethylation using a suitable ethylating agent.

Chromogenic recording materials using the fluoran compound of the invention as a chromogenic substance are, for example, pressure-sensitive copying papers, heat-sensitive recording papers, heat-sensitive copying papers, electrothermo recording papers, toners for electrophotography, stamping inks, ribbons for typewriter and the like but are not limited only thereto. For the manufacture of pressure-sensitive copying papers using the fluoran compound of the invention, methods as disclosed in U.S. Pat. Nos. 2,548,366 and 2,800,458 are conveniently used in the practice of the invention. For the heat-sensitive recording materials such as heat-sensitive recording papers or heat-sensitive copying papers, methods as described in Japanese Patent Publication Nos. 6040/1965, 4160/1968 and 14039/1970 can be suitably used. Moreover, toners for electrophotography may be prepared, for example, according to the method as described in Japanese Laid-open Patent Application No. 56932/1977. For the electro-thermo recording papers, there are used methods described, for example, Japanese Laid-open Patent Application Nos. 96137/1973 and 101935/1973 and Japanese Patent Publication No. 10193/1981. In practice, the fluoran compound may be used in combination with other chromogenic substances.

PREPARATION 1 (PREPARATION OF BENZOIC ACID DERIVATIVES)

48.3 g of m-N-isobutylethylaminophenol and 37.8 g of phthalic anhydride were added to 100 ml of tetrachloroethylene, which was heated under reflux while agitating for 5 hours. Thereafter, 20.0 g of caustic soda was dissolved in 260 ml of water and added to the reaction system, followed by refluxing under agitation for 10 minutes and allowing the system to stand thereby extracting the resulting benzoic acid derivatives as the sodium salt in the aqueous phase. To the extract, after washing with tetrachloroethylene, was added 38 ml of concentrated hydrochloric acid to render the system acidic, followed by extracting a separated oily material with 160 ml of hot tetrachloroethylene. The extract was washed with a small amount of hot water and cooled with agitation, whereupon the benzoic acid derivative precipitated giving a slurry as a whole. After cooling to about 40° C. the resulting precipitate was collected by filtration and washed with a small amount of tetrachloroethylene, followed by recrystallizing from toluene by the use of active carbon to obtain 56.8 g (yield 66.4%) o-(4-N-isobutylethylamino-2-hydroxybenzoyl)benzoic acid (formula V) having a melting point of 141.6° to 142.4° C. in the form of substantially colorless crystals.

The m-N-isobutylethylaminophenol used as the starting material in this preparatory experiment was prepared as follows. Resorcin and isobutylamine were heated in the presence of anhydrous zinc chloride at a temperature of 140° to 160° C. to give m-siobutylaminophenol (boiling point: 140° to 145° C./4.2 mmHg). The m-isobutylaminophenol was N-ethylated with a slightly excess amount of diethyl sulfate at a temperature of about 60° C. in toluene admixed with half as much water as the toluene by the use of sodium hydrogencarbonate for neutralization. As a result, an oily substance of the m-N-isobutylethylaminophenol having a boiling point of 130° to 135° C./3.5 mmHg was obtained.

PREPARATION 2 (PREPARATION OF FLUORAN COMPOUND)

20.0 g of o-(4-N-isobutylethylamino-2-hydroxybenzoyl)benzoic acid prepared in Preparation 1 and 14.7 g of 4-ethoxy-2-methyldiphenylamine were charged into 97 g of concentrated sulfuric acid and stirred at a temperature of 20° to 25° C. for 48 hours. The mixture was poured into iced water and the resulting precipitate was collected by filtration. The filter cake was dispersed in water, to which was added an aqueous caustic soda solution to render the system alkaline. The dispersion was again filtered, washed with water and recrystallized from n-butanol to obtain 21.0 g of 3-N-isobutylethylamino-6-methyl-7-phenylaminofluoran (yield from the benzoic acid derivative: 68%) having a melting point of 150° to 153.5° C. in the form of slightly brown, fine crystals.

EXAMPLE 1

3.5 g of 3-N-isobutylethylamino-6-methyl-7-phenylaminofluoran, 15 g of clay ("UW-90", manufactured by Engelhard Inc. U.S.A.), 41.5 g of a 15% aqueous solution of polyvinyl alcohol (Kuraray Poval, PVA-105, manufactured by Kuraray Co., Ltd. Japan) and 40.0 g of pure water were placed in a 250 ml polyethylene bottle along with 150 g of glass beads (diameter: 1 to 1.5 mm) and stoppered. Subsequently, the bottle was placed on a paint conditioner, by Red Devil Co., Ltd., and shaked for 6 hours at 630 vibrations per minute. The glass beads were removed to obtain an aqueous viscous suspension containing particles of 3-N-isobutylethylamino-6-methyl-7-phenylaminofluoran with a size of 2 to 3 microns.

On the other hand, 10.5 g of bisphenol A, 8.0 g of clay as used above, 41.5 g of a 15% aqueous solution of polyvinyl alcohol as used above and 40.0 g of pure water were placed in a 250 ml polyethylene bottle along with glass beads (diameter: 1 to 1.5 mm) and stoppered, followed by setting on a paint conditioner of Red Devil Co., Ltd. After shaking of the mixture at 630 vibrations per minute for 10 hours, the glass beads were removed to obtain an aqueous suspension containing particles of bisphenol A with a size of 2 to 3 microns.

To the aqueous bisphenol A suspension was added the aqueous suspension of 3-N-isobutylethylamino-6-methyl-7-phenylaminofluoran, followed by sufficient agitation for 30 minutes for mixing. The mixture was manually coated onto a white paper by the use of wire rod No. 12 and dried by hot air of 60° C. for 3 minutes. As a result, there was obtained a very white heat-sensitive recording paper which had little soil or stain on the coated surface thereof. This recording paper developed slightly reddish black color very quickly upon heating with a heat stylus, heat type or heat pattern.

This heat-sensitive recording paper was subjected to a color formation test using a Dry Heating Tester (manufactured by Kishino Science Machinery Co., Ltd.) by heating the paper on both sides thereof for 5 seconds at temperatures of 70° C., 80° C., 85° C., 90° C., 95° C., 100° C., 105° C., and 110° C. and 140° C., thereby developing a slightly reddish black color. The color density of the developed side was measured by the Macbeth reflection densitometer RD-514 (Wratten filter #106). The results are shown in Table 1 at the column of compound I.

COMPARATIVE EXAMPLE 1

The general procedure of Example 1 was repeated except that there were used 3-diethylamino-6-methyl-7-phenylaminofluoran, 3-N-cyclohexylmethylamino-6-methyl-7-phenylaminofluoran and 3-N-iso-pentylethylamino-6-methyl-7-phenylaminofluoran instead of 3-N-isobutylethylamino-6-methyl-7-phenylaminofluoran, thereby making heat-sensitive papers. These papers were subjected to color development and measurement of the color density in the same manner as in Example 1. The color densities of the respective papers are indicated in Table 1 at columns of compounds II, III and IV, respectively. The coated surfaces of these heat-sensitive recording papers were observed to be more soiled than the paper made in Example 1.

EXAMPLE 2

The general procedure of Example 1 was repeated using benzyl p-hydroxybenzoate instead of the bisphenol A, thereby making a heat-sensitive recording paper. The paper was thermally developed in the same manner as in Example 1 at temperatures of 70° C., 75° C., 80° C., 85° C., 90° C., 95° C. and 100° C. The developed surfaces were subjected to the measurement of the color density. The results are indicated in Table 2 at the column of compound I. The developed surface assumed pure black.

COMPARATIVE EXAMPLE 2

The general procedure of Example 2 was repeated except that there were used 3-diethylamino-6-methyl-7-phenylaminofluoran, 3-N-cyclohexylmethylamino-6-methyl-7-phenylaminofluoran and 3-N-isopentylethylamino-6-methyl-7-phenylaminofluoran instead of 3-N-isobutylethylamino-6-methyl-7-phenylaminofluoran, thereby making heat-sensitive recording papers. The papers were each subjected to color development and measurement of the color density on the color-developed surface thereof. The results are indicated in Table 2 at the columns of compounds II, III and IV, respectively. The developed color of these compounds were slightly greenish black.

EXAMPLE 3

1.0 g of 3-N-isobutylethylamino-6-methyl-7-phenylaminofluoran was dissolved in 20 g of an alkylnaphthalene by heating to 90° C. (solution A). On the other hand, 2.0 g of gelatin (isoelectric point: 8.0) and 0.5 g of carboxymethyl cellulose were completely dissolved in 120 ml of water (solution B). Thereafter, the solutions A and B were mixed together at 50° to 60° C. and emulsified by high speed agitation, followed by adjusting the pH to 8.5 to 9.0. After the adjustment of the pH, the emulsion was agitated at high speed for further 20 minutes and the pH was gradually lowered with diluted acetic acid to 3.8. While agitating, the mixture was cooled to 5° to 10° C., to which was added 6 g of a formalin solution (37%), followed by agitation at 10° to 20° C. for further 1 hour.

Next, a sodium hydroxide solution (5%) was added to the emulsion to adjust the pH to 9.0. The emulsion was gently agitated for further several hours to give an emulsion containing very fine capsules. Each fine capsule had a gel film covering made from carboxymethyl cellulose and gelatin, containing therein the alkylnaphthalene solution of 3-N-isobutylethylamino-6-methyl-7-phenylaminofluoran.

The emulsion was coated onto a sheet of paper and dried to obtain a coated back paper (CB) of pressure-sensitive copying paper. On the other hand, an aqueous suspension of phenol-formaldehyde resin was coated onto a paper sheet and dried to obtain a coated front paper (CF). The coated surface of the CB was superposed on the coated surface of the CF, and on the CB characters or letters were written. Black characters or letters appeared very quickly on the coated surface of the CF.

When clay was ued instead of the phenol-formaldehyde resin to obtain a CF, purplish black characters appeared.

EXAMPLE 4

The general procedure of Example 1 was repeated using 4-hydroxy-4-methyldiphenyl sulfone instead of bisphenol A as the developer, thereby making a heat-sensitive recording paper.

Similarly, another heat-sensitive recording paper was made using 4-hydroxy-4'-isopropoxydiphenyl sulfone instead of bisphenol A. These recording papers were developed using the same procedure and apparatus as used in Example 1 in order to measure the resulting black color density. The results are shown in Table 3 below.

TABLE 3

| Developer | Color Formation Temperature (°C.) | | | | | | |
|---|---|---|---|---|---|---|---|
| | 70 | 75 | 80 | 85 | 90 | 95 | 100 |
| 4-Hydroxy-4')-methyl-diphenyl sulfone | 0.24 | 0.38 | 0.65 | 1.19 | 1.27 | 1.31 | 1.31 |
| 4-Hydroxy-4'-isopropoxy-diphenyl sulfone | 0.21 | 0.34 | 0.59 | 1.12 | 1.24 | 1.28 | 1.30 |

EXAMPLE 5

7.0 g of 3N-isobutylethylamino-6-methyl-7-phenylaminofluoran, 11.5 g of clay (as used in the foregoing examples), 41.5 g of a 15% aqueous solution of polyvinyl alcohol (as used in the foregoing examples) and 40.0 g of pure water were treated in the same manner as in Example 1, thereby giving an aqueous suspension of the fluoran compound (suspension A).

On the other hand, 7.0 g of dibenzyl terephthalate (sensitizer), 11.5 g of clay (as used in the foregoing examples), 41.5 g of a 15% aqueous solution of polyvinyl alcohol (as used in the foregoing examples) and 40.0 g of pure water were treated in the same manner as described above, thereby obtaining an aqueous suspension of dibenzyl terephthalate (suspension B).

10.5 g of bisphenol A, 8.0 g of clay (as used above), 41.5 g of a 15% aqueous solution of polyvinyl alcohol (as used above) and 40.0 g of pure water were treated in the same manner as described above, thereby obtaining an aqueous suspension of bisphenol A (suspension C).

Moreover, the above procedure was repeated using, instead of bisphenol A, benzyl 4-hydroxybenzoate, 4-hydroxy-4'-methyldiphenyl sulfone and 4-hydroxy-4'-isopropoxydiphenyl sulfone to obtain suspensions D, E and F, respectively.

1 part of the suspension A, 1 part of the suspension B and 2 parts of the suspension C were mixed together; 1 part of the suspension A, 1 part of the suspension B and 2 parts of the suspension D were mixed together; 1 part of the suspension A, 1 part of the suspension B and 2 parts of the suspension E were mixed together; and 1 part of the suspension A, 1 part of the suspension B and 2 parts of the suspension F were mixed. Thus, four coating suspensions were prepared.

The respective suspensions were coated onto white papers in the same manner as in Example 1 and dried to give heat-sensitive recording papers (designated as heat-sensitive papers C, D, E and F, respectively).

These papers were developed and subjected to measurement of the color density (black) in the same manner as in Example 1. The measured values are shown in Table 4.

TABLE 4

| Heat-sensitive Recording Paper | Developer | Color Formation Temperature (°C.) | | | | | | |
|---|---|---|---|---|---|---|---|---|
| | | 70 | 75 | 80 | 85 | 90 | 95 | 100 |
| C | Bisphenol A | 0.30 | 0.44 | 0.69 | 0.92 | 1.08 | 1.16 | 1.20 |
| D | Benzyl 4-hydroxybenzoate | 0.44 | 1.10 | 1.26 | 1.31 | 1.33 | 1.34 | 1.33 |
| E | 4-Hydroxy-4'-methyldiphenyl sulfone | 0.35 | 0.78 | 1.19 | 1.26 | 1.31 | 1.32 | 1.32 |
| F | 4-Hydroxy-4'-isopropoxydiphenyl sulfone | 0.31 | 0.64 | 1.14 | 1.23 | 1.28 | 1.30 | 1.31 |

What is claimed is:

1. A chromogenic recording material comprising 3-N-isobutylethylamino-6-methyl-7-phenylaminofluoran, an acidic substance capable of causing the color formation of said fluoran compound and a substrate which supports the fluoran compound the acidic substance on its surface.

2. The chromogenic recording material according to claim 1, wherein said chromogenic recording material is a pressure-sensitive copying paper.

3. The chromogenic recording material according to claim 1, wherein said chromogenic recording material is a heat-sensitive recording paper.

4. The chromogenic recording material according to claim 3, wherein the acidic substance is bisphenol A.

5. The chromogenic recording material according to claim 3, wherein the acidic substance is benzyl 4-hydroxybenzoate.

6. The chromogenic recording material according to claim 3, wherein the acidic substance is 4-hydroxy-4-methyldiphenyl sulfone.

7. The chromogenic recording material according to claim 3, wherein the acidic substance is 4-hydroxy-4'-isopropoxydiphenyl sulfone.

8. The chromogenic recording material according to any one of claims 3 to 7, further comprising dibenzyl terephthalate as a sensitizer.

9. The chromogenic recording material according to any one of claims 3 to 7, further comprising dibenzyl isophthalate as a sensitizer.

* * * * *